US010786163B2

(12) United States Patent
Chang et al.

(10) Patent No.: US 10,786,163 B2
(45) Date of Patent: Sep. 29, 2020

(54) BLOOD PRESSURE MEASUREMENT DEVICES AND METHODS

(71) Applicant: Cardio Ring Technologies, Inc., San Jose, CA (US)

(72) Inventors: Kuang-Fu Chang, Taichung (TW); Yu-Chi Wang, Taipei (TW); Leng-Chun Chen, Hsinchu (TW); Jun-Ming Chen, Bethesda, MD (US); Wen-Pin Shih, Taipei (TW)

(73) Assignee: Cardio Ring Technologies, Inc., San Jose, CA (US)

( * ) Notice: Subject to any disclaimer, the term of this patent is extended or adjusted under 35 U.S.C. 154(b) by 0 days.

(21) Appl. No.: 16/427,585

(22) Filed: May 31, 2019

(65) Prior Publication Data

US 2019/0365258 A1    Dec. 5, 2019

Related U.S. Application Data

(60) Provisional application No. 62/679,418, filed on Jun. 1, 2018.

(51) Int. Cl.
| A61B 5/02 | (2006.01) |
| A61B 5/021 | (2006.01) |
| A61B 5/11 | (2006.01) |
| A61B 5/00 | (2006.01) |
| A61B 5/022 | (2006.01) |

(52) U.S. Cl.
CPC ........ *A61B 5/02141* (2013.01); *A61B 5/1126* (2013.01); *A61B 5/6826* (2013.01); *A61B 5/6838* (2013.01); *A61B 5/021* (2013.01); *A61B 5/022* (2013.01); *A61B 5/02108* (2013.01); *A61B 5/681* (2013.01); *A61B 5/6824* (2013.01); *A61B 5/6831* (2013.01); *A61B 2562/0247* (2013.01); *A61B 2562/0261* (2013.01)

(58) Field of Classification Search
CPC . A61B 5/02141; A61B 5/6826; A61B 5/6838; A61B 5/1126; A61B 2562/0261; A61B 5/022; A61B 5/021; A61B 5/681; A61B 5/6824; A61B 5/6831; A61B 5/02108; A61B 2562/0247
See application file for complete search history.

(56) References Cited

U.S. PATENT DOCUMENTS 2,943,486 A * 7/1960 Osgood ............... G01F 1/28
                                              73/861.74
3,154,066 A * 10/1964 Grindheim ........ A61B 5/02444
                                              600/501

(Continued)

FOREIGN PATENT DOCUMENTS

| WO | WO 2015/070343 | 5/2015 |
| WO | WO 2015/193045 | 12/2015 |

(Continued)

*Primary Examiner* — Navin Natnithithadha
*Assistant Examiner* — Andrey Shostak
(74) *Attorney, Agent, or Firm* — Levine Bagade Han LLP (57) ABSTRACT

Devices and methods for monitoring blood pressure with a wearable device, which includes a contact member that concentrates radially directed tissue movement produced by arterial motion into a relatively small spot to compress the strain device. This concentration significantly increases the sensitivity of the force detecting device and allows further miniaturization of the device.

22 Claims, 10 Drawing Sheets

(56) References Cited

U.S. PATENT DOCUMENTS

| | | | |
|---|---|---|---|
| 4,331,154 A | 5/1982 | Broadwater et al. | |
| 4,993,422 A | 2/1991 | Hon et al. | |
| 5,406,952 A | 4/1995 | Barnes et al. | |
| 6,360,615 B1 | 3/2002 | Smela | |
| 7,547,282 B2 | 6/2009 | Lo et al. | |
| 9,501,735 B2 | 11/2016 | Proud et al. | |
| 2007/0287923 A1* | 12/2007 | Adkins | A61B 5/412 600/485 |
| 2008/0167535 A1 | 7/2008 | Stivoric et al. | |
| 2014/0206955 A1 | 7/2014 | Stivoric et al. | |
| 2014/0221784 A1 | 8/2014 | Pacione et al. | |
| 2014/0288438 A1 | 9/2014 | Venkatraman et al. | |
| 2015/0193045 A1 | 7/2015 | Zhou et al. | |
| 2015/0289797 A1 | 10/2015 | Pacione et al. | |
| 2015/0305632 A1 | 10/2015 | Najarian et al. | |
| 2015/0366504 A1 | 12/2015 | Connor | |
| 2015/0374245 A1* | 12/2015 | Szilagyi | A61B 5/14551 600/479 |
| 2016/0150362 A1 | 5/2016 | Shaprio et al. | |
| 2017/0086686 A1 | 3/2017 | Narasimhan et al. | |
| 2017/0089782 A1* | 3/2017 | Hirt | A61B 5/681 |
| 2017/0340209 A1 | 11/2017 | Klaassen et al. | |
| 2018/0049655 A1 | 2/2018 | Melnkowycz et al. | |
| 2018/0061203 A1 | 3/2018 | Shaprio et al. | |
| 2018/0078154 A1 | 3/2018 | Knickerbocker et al. | |

FOREIGN PATENT DOCUMENTS

| | | |
|---|---|---|
| WO | WO 2018/005298 | 1/2018 |
| WO | WO 2019/232300 | 12/2019 |

\* cited by examiner

BLOOD PRESSURE MEASUREMENT DEVICES AND METHODS

CROSS-REFERENCE TO RELATED APPLICATIONS

This application is a non-provisional of U.S. provisional application 62/679,418 filed on Jun. 1, 2018, the content of which is incorporated herein by reference in its entirety.

BACKGROUND OF THE INVENTION

Cardiovascular disease (CVD) accounts for approximately a significant number of deaths on a world-wide basis. CVD includes coronary heart disease (CHD), which accounts for the majority of CVD deaths, as well as stroke and heart failure. Many more individuals carry a diagnosis of CVD and live with the diagnosis. Those living with CVD are at risk of acute heart attack, strokes and other chronic conditions that can adversely affect the individual's quality of life over a long-term. Ultimately, CVD increases the risks of mortality in the patient. Therefore, there is a keen interest by governments, healthcare providers, as well as the general population to prevent CVD The rise of portable smart-devices, such as smart phones, smart watches, fitness monitors, etc. has given individuals a useful tool to monitor health parameters to address CVD symptoms, where such health parameters include blood pressure and heart rate. Such devices are also of interest to healthy individuals so that who can monitor such data to avoid the onset or progression of CVD.

Non-invasive blood pressure measuring devices including sphygmomanometers and photoplethysmography are used in monitoring patient's blood pressures to prevent various cardiovascular diseases or provide doctors with early diagnosis. However, most of them are bulky and heavy which are inconvenient for outdoor applications and long-time monitoring. Previously, wearable blood-pressure monitoring devices that allowed for real-time monitoring and portable capability are described in US20180049655 and WO2018005298, the entirety of each of which is incorporated by reference. However, there remains a need to more accurately measure blood pressure using a portable, non-obtrusive device.

BRIEF SUMMARY OF THE INVENTION

The present disclosure includes a force detecting device relies on a contact member that concentrates radially directed tissue movement produced by arterial motion into a relatively small spot to compress the strain device. This concentration significantly increases the sensitivity of the force detecting device and allows further miniaturization of the device. By increasing the sensitivity with the contact member, the device can be compressed on user's skin with a smaller area being held tight against the tissue. This relatively small surface area bringing more comfort to the user. The contact member of the current is designed in such a way that the radial motion of tissue is more prominent than movement of tissue in other directions. This allows suppression of any undesirable signals, such as signals from friction or uneven motion of the tissue. The contact member also protects the strain device from damages due to large contact force and friction from user. By radial direction, it is meant in a direction radially away from the vessel being monitored.

The present disclosure includes devices for monitoring blood pressure in a blood vessel using a tissue adjacent to the blood vessel. For example, such a device includes a device body configured to extend at least partially about the digit, the device body having an interior surface adapted to be positioned adjacent or in contact with a surface of the digit; a tissue movement detecting assembly positioned on or in the device body, the transducer assembly comprising a strain device; a contact member having a tissue engaging surface protruding beyond the interior surface of the device body such that when the device body is positioned adjacent to tissue, the contact member compresses the tissue, the contact member also having a strain inducing surface adjacent to the transducer assembly; and wherein the contact member comprises a perimeter region and a central region, where the central region is configured to transmit displacement of the contact member such that, when the tissue engaging surface engages the tissue, displacement of tissue in a radial direction relative to the tissue caused by a change in a pressure in the blood vessel also displaces the tissue engaging surface causing displacement of the central region of the contact member in the radial direction so that the strain inducing surface alters a strain in the strain device to produce a change in an electrical property of the strain device.

In another variation, the contact member comprises a double layer structure having a first layer adjacent to the tissue engaging surface and a second layer spaced from the first layer, where the first and second layer are joined by a central region of the contact member.

The device body can optionally include a cavity that nests the contact member. Variations of the device include one or more power supplies electrically coupled to the transducer assembly.

In one variation of the device the contact member is configured such that the perimeter region of the contact member is reinforced such that the perimeter region transmits displacement less than the central region of the contact member.

Variations of the contact member are configured such that the perimeter region of the contact member is weakened to cause the central region to displace in the radial direction by flexure of the perimeter region. For example, perimeter region of the contact member can be softer than the central region such that the central region transmits displacement greater than the perimeter region. In additional variations, the contact member comprises at least one cavity below the tissue engaging surface, where the at least one cavity extends about the central region, wherein the at least one cavity causes the perimeter region of the contact member to be softer relative to the central region which improves an ability of the central region to transmit displacement.

Variations of the device include strain inducing surfaces that comprise at least one protrusion, wherein displacement of the central region of the contact member causes the at least one protrusion to alter the strain in the strain device. The at least one protrusion can comprise a plurality of protrusions.

Variations of the devices can further include one or more displacement limiting structures that can limit movement of the strain inducing surface or can limit movement of the strain device.

In an additional variation, a device can include a transducer assembly comprises a deformable base adjacent to the strain device, where the deformable base permits deformation of the strain device. The deformable base can comprise an elastomer that can be elastically deformable. In addition, variations of the device can include protrusion(s) adjacent, inside, or through the deformable base that increases deflection of the strain device.

In another variation of the device, the transducer assembly and contact member form a primary sensor, the device further comprising a secondary sensor comprising a second contact member and a second transducer assembly, wherein the secondary sensor is spaced a distance from the primary sensor on the interior surface of the device body.

The strain devices used herein can comprise at least a strain gauge or a conductive polymer. In one variation, the strain device comprises a first strain gauge and a second strain gauge. For example, the first strain gauge can be positioned on a first side of a deflectable base and where the second strain gauge can be positioned on a second side of a deflectable base, where a fixed end of the deflectable base is coupled to an anchoring structure and a free end of the deflectable base is positioned adjacent to the strain inducing surface.

The device body can comprise a shape selected from a group consisting of a cylinder shape, a partial cylinder shape, a ring shape, an oval shape, and a non-cylinder shape.

The device body can optionally include a biasing member configured to bias the device body against the digit to cause the contact member to at least engage tissue of the digit. In an additional variation, the biasing member comprises a mechanism selected from the group comprising a spring, a gasket, a screw, a soft polymer, and a combination thereof.

The present disclosure also includes methods for monitoring blood pressure in a blood vessel within a tissue using any of the devices described herein. For example, such a method can include positioning a device body adjacent to the tissue, where the device body comprises a contact member coupled to a transducer assembly with the contact member protruding from an interior surface of the device body; wherein the contact member comprises a tissue engaging surface protruding above the interior surface of the device body such that, when the device body is positioned adjacent to the tissue the contact member compresses a tissue in the digit, the contact member also having a strain inducing surface adjacent to the transducer assembly, where a central region of the contact member transmits displacement of the tissue in the digit to the transducer assembly at a greater degree than a perimeter portion of the contact member; generating a signal in the transducer assembly caused by a movement of the central portion of the contact member against the transducer assembly and in response to movement of the tissue caused by a pulsatile flow in the blood vessel; and transmitting the signal to a processing unit that is configured to calculate a blood pressure of the vessel from the signal.

The methods can include transmitting wirelessly. Variations of the method can comprise continuously transmitting the signal or transmitting the signal periodically.

The method can further include recording the signal on a storage device to generate a series of recorded signals on the storage device.

In another variation of the device, the device body further includes a second contact member coupled to a second transducer assembly, wherein the second contact member is spaced circumferentially away from the first contact member, the method further comprises generating a second signal in the transducer assembly caused by movement of a central portion of the second contact member against the second transducer assembly in response to movement of the tissue in the digit.

A variation of the method further comparing the first signal to the second signal to generate a rotation indicator signal. In another variation, the rotation indicator signal can inform a user to rotate the device body relative to the tissue.

In another variation, the method includes comparing the first signal to the second signal to generate a device tightness signal. The method can also include providing the tightness indicator signal to a user to inform the user to adjust the device tightness adjacent to the tissue.

The method can further include using an oscillometric blood pressure cuff to calibrate the blood pressure calculation.

Another variation of the device described herein includes a device for monitoring blood pressure in a blood vessel using a tissue adjacent to the blood vessel. For example, the device can include a device body; a tissue movement detecting assembly positioned on or in the device body, the transducer assembly comprising a strain device; a contact member having a tissue engaging surface protruding beyond a surface of the device body such that when the device body is positioned adjacent to tissue, the contact member compresses the tissue, the contact member also having a strain inducing surface adjacent to the transducer assembly; and wherein the contact member comprises a perimeter region and a central region, where the central region is configured to transmit displacement of the contact member such that, when the tissue engaging surface engages the tissue, displacement of tissue in a radial direction relative to the tissue caused by a change in a pressure in the blood vessel also displaces the tissue engaging surface causing displacement of the central region of the contact member in the radial direction so that the strain inducing surface alters a strain in the strain device to produce a change in an electrical property of the strain device.

In one variation of the device the device body comprises a blood pressure cuff. Alternatively, the device body can comprise a pulse oximeter.

This application is related to PCT application number PCT/US2019/034803, filed on May 31, 2019, the entirety of which is incorporated by reference.

DETAILED DESCRIPTION OF THE INVENTION

Methods and devices are described herein that relate to monitoring blood pressure in a vessel of a region of tissue. The methods and devices described herein can monitor blood pressure in a digit of a hand or in other areas of the body where the pulsatile flow of blood in a vessel displaces adjacent tissue that can be detected from a surface of the tissue. In addition, the methods and devices disclosed herein include improvements for detecting movement in a tissue of a region of the body, where the movement in the tissue arises from blood pressure changes within a vessel in that tissue. Optionally, the devices and methods described herein can be used wearable devices and non-invasive monitoring blood-pressure in real-time.

Figure 1A:
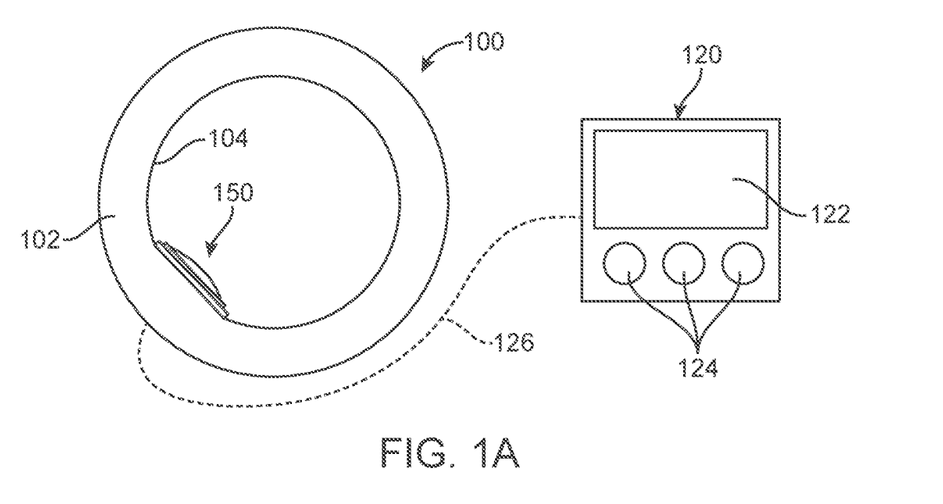
FIGS. 1A and 1B illustrate respective front and oblique views of an example of a device configured to monitor blood pressure using movement in tissue that is driven by the blood flow within a vessel located in that tissue.
Figure 1B:
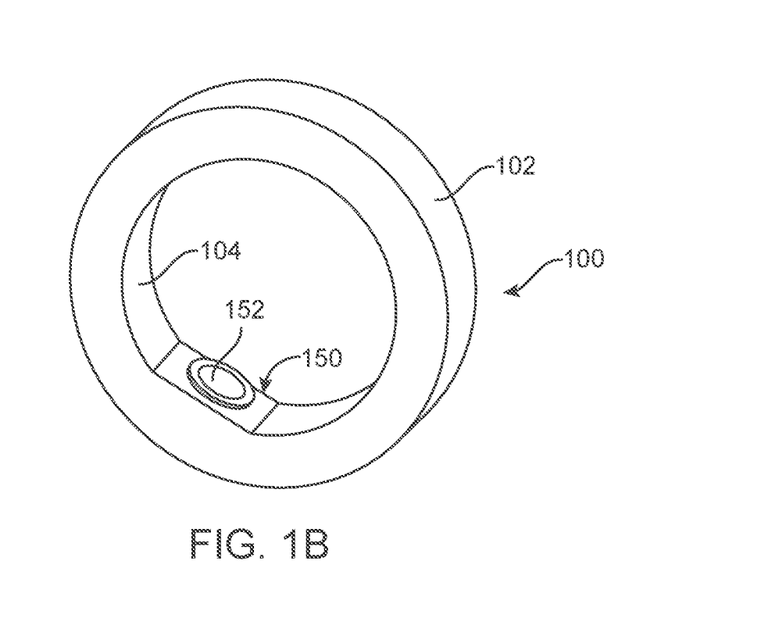

FIGS. 1A and 1B illustrate respective front and oblique views of an example of a device 100 configured to monitor blood pressure using movement in tissue that is driven by the blood flow within a vessel located in that tissue. In the examples illustrated in FIGS. 1A and 1B, the illustrated variation of the device 100 is configured with a ring-shaped body 102 that houses a tissue displacement measuring apparatus 150 having a portion that protrudes from an inner surface 104 of the ring shaped body 100. This variation is suited for placement about a digit of an individual's hand such that it can detect movement of tissue in the digit that is caused by pulsatile flow of a vessel within the digit/tissue. However, additional variations of a blood pressure monitoring apparatus under the present disclosure are not limited to ring-type devices. The movement detecting apparatus 150 The device also can simply monitor movement of tissue in the digit, where the tissue movement can be caused by the oscillation of the blood vessel due to pressure changes therein. As shown, the device 100 can communicate 126 (either via a wire, wireless connection, cloud-based transmission, etc.) to a user interface 120. The user interface 120 can comprise a body wearable apparatus or can comprise a computer, smart-phone, tablet, or other electronic apparatus. Variations of the user interface 120 can include a feedback portion 122 (either visual, audible, etc.) and/or controls 124.

FIG. 1B shows a perspective view of the device 100 of FIG. 1A. As shown, the ring-shaped body 102 includes an inner surface 104 that can be positioned about a digit of an individual. The ring-shaped body 102 houses an assembly 150 that detects movement of tissue using a contact member 152 that transmit movement of tissue adjacent to the contact member into the assembly 150 (as will be discussed below). The contact member 152 can extend beyond an inner surface 104 of the ring-body 102. The degree of extension of the contact member 152 can vary depending upon the application. The illustration is intended to convey the principles of the device. Furthermore, while the illustrated variation only shows a single assembly 150, variations of the device can include any number of additional assemblies spaced at any interval along the body of the device 100.

The tissue contact member 152 can comprise an elastomer that is softer than a body of the device. That is, the Young's modulus of the elastomer should be smaller than the Young's modulus of the ring body 102. In such configuration, stretching of or compression to the contact member 152 mainly deforms the elastomer rather than the ring body itself. For example, elastomers suitable for a wearable device can include, but are not limited to natural rubber, Silicone, Neoprene, Polyurethanes, Polybutadiene, etc. In one variation, the elastomer comprises polydimethylsiloxane (PDMS) with different desired mix ratio. However, the present invention is not limited thereto, and any materials with elastomeric characteristic compared to the ring body can be used in the devices disclosed herein.

Figure 2A:
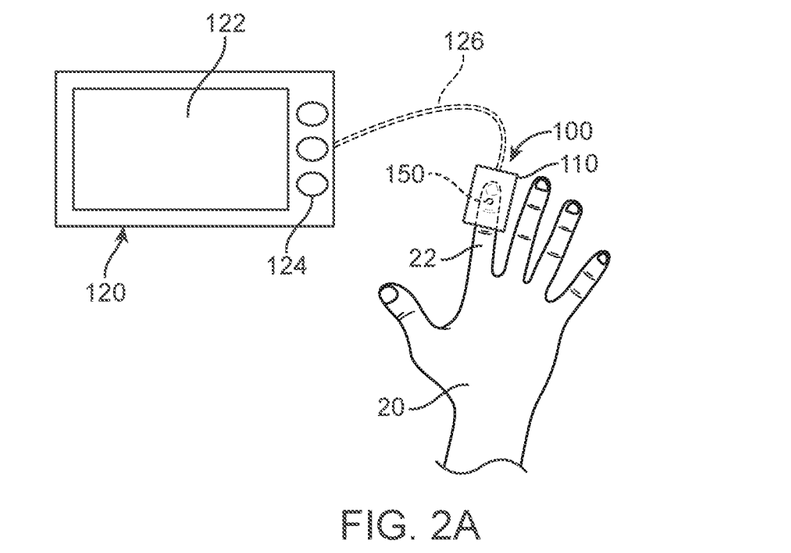
FIGS. 2A and 2B illustrate additional variations of tissue displacement assemblies 150 for use with additional variations of blood pressure measuring devices.
Figure 2B:
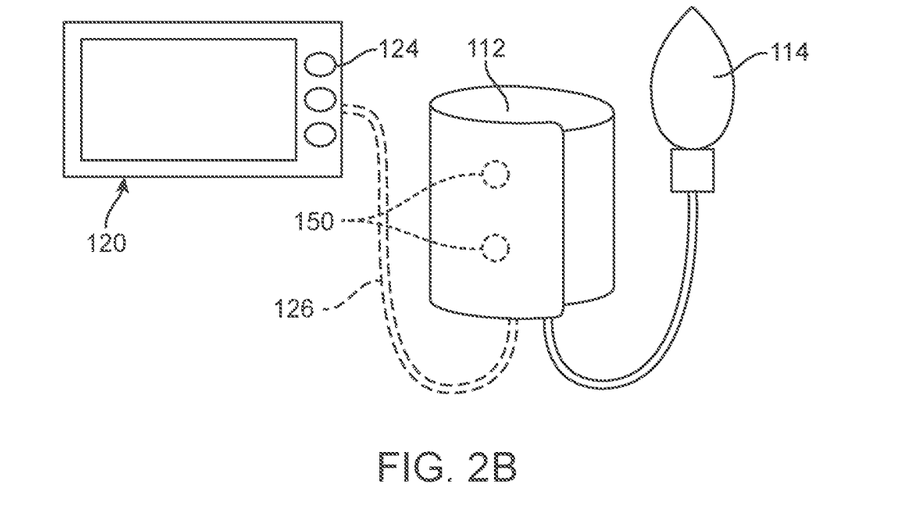

FIGS. 2A and 2B illustrate additional variations of tissue displacement assemblies 150 for use with additional variations of blood pressure measuring devices 100. The variation shown in FIG. 2A illustrates a finger cuff or cradle 110 that houses one or more assemblies 150. As shown, a finger 22 of a hand 20 is positioned within or on the device body 110 such that the assembly 150 can detect movement of tissue and transmit (via a wired or wireless connection 126) to a user interface device 120 (as described above). FIG. 2B illustrates a traditional blood pressure cuff 122 having a pump or bladder 114 that is used to secure the cuff 112 about a leg or arm of a patient. The cuff 112 includes any number of assemblies 150 that can measure displacement of tissue due to pulsatile flow of blood in a vessel within the tissue that is adjacent to the cuff 112.

Figure 3A:
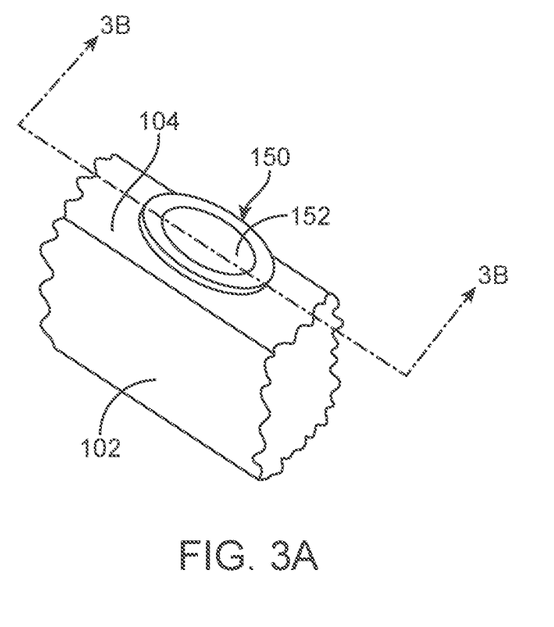
FIG. 3A illustrates a partial view of a body of the device shown in FIGS. 1A and 1B for illustrating a variation of a movement detecting apparatus.

FIG. 3A illustrates a partial view of a body 102 of the device shown in FIGS. 1A and 1B for purposes of illustrating one variation of a movement detecting apparatus 150 that can be used with any of the blood pressure detecting devices described herein. In this example, the apparatus 150 is positioned within the ring-shaped device body 102, where the movement detecting apparatus includes a contact member 152 that extends beyond a tissue facing surface 104 of the ring body 102.

Figure 3B:
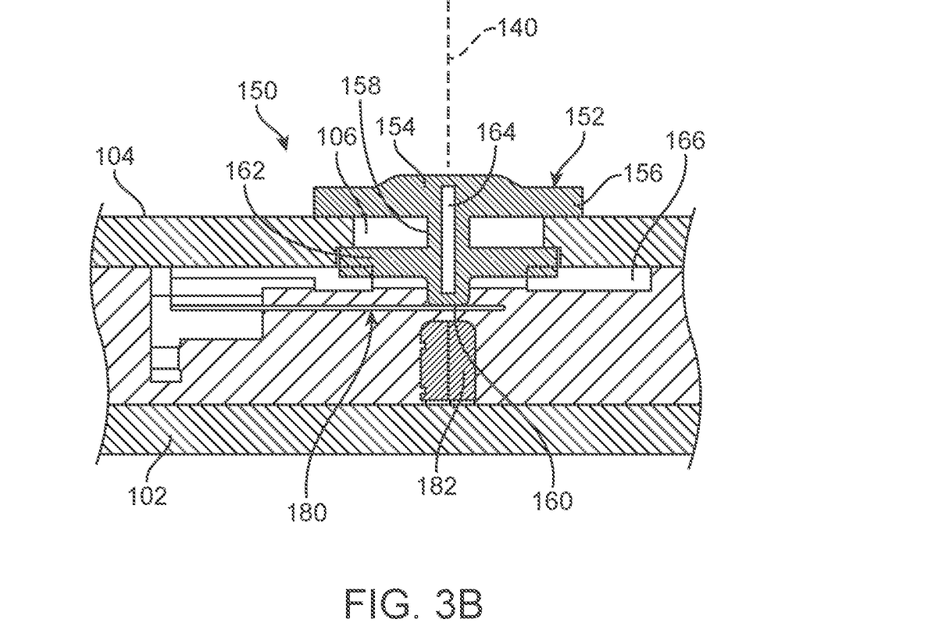
FIG. 3B represents a cross sectional view of the movement detecting device of FIG. 3A taken along the line 3B-3B.

FIG. 3B represents a cross sectional view of the movement detecting device 150 of FIG. 3A taken along the line 3B-3B. As shown, the device 150 includes a contact member 152 that has a tissue engaging surface 154 protruding beyond the interior surface 104 of the device body 102 such that when the device body is positioned adjacent to tissue, the contact member compresses the tissue or is positioned in contact with tissue. In this variation, the tissue engaging surface 154 includes a perimeter region 156 that engages the inner surface 104 while the tissue engaging surface 154 is positioned adjacent to a cavity 106 or recess within the inner surface 104 of the device body. As described below, the cavity 106 assists in permitting displacement of the tissue engaging surface 154 (as a result of tissue displacement or a pressure wave caused by tissue movement). In this variation, the tissue engaging surface 154 extends above the perimeter region 156 to assist in transmitting displacement of the tissue. However, variations of devices can include perimeter regions that are flush with the tissue engaging surface. It is noted that a power supply can be positioned within the monitoring unit/display. Alternatively, a power supply (e.g., a battery, rechargeable battery, or other power source) can be positioned within the housing 104 of the device.

The tissue engaging surface 154 is adjacent to a central region 158 that transmits displacement of the tissue engaging surface 154 to a strain inducing surface 160. Therefore, displacement of the tissue engaging surface 154 causes displacement of the strain inducing surface 160. The strain inducing surface 160 is adjacent to/in contact with a strain device 180 where the displacement can be measured by the strain device 180. The central region 158 can include a strain inducing surface 160 as well as a second perimeter region 162 that engages a portion of the body 102. Moreover, a stop or displacement limiting structure 182 can limit displacement of the strain device 180. FIG. 3B also illustrates a variation of the movement detecting apparatus 150 as having an optional stiffening member 164 positioned within the contact member 152. The design of the contact member 152 increases the ability of the contact member 152 to transmit radial movement (i.e., movement that is parallel to a central axis 140) of the contact member 152. The apparatus 150 can also include any number of support structures 166 that maintains the contact member 152 securely within the body 102 structure.

Figure 4A:
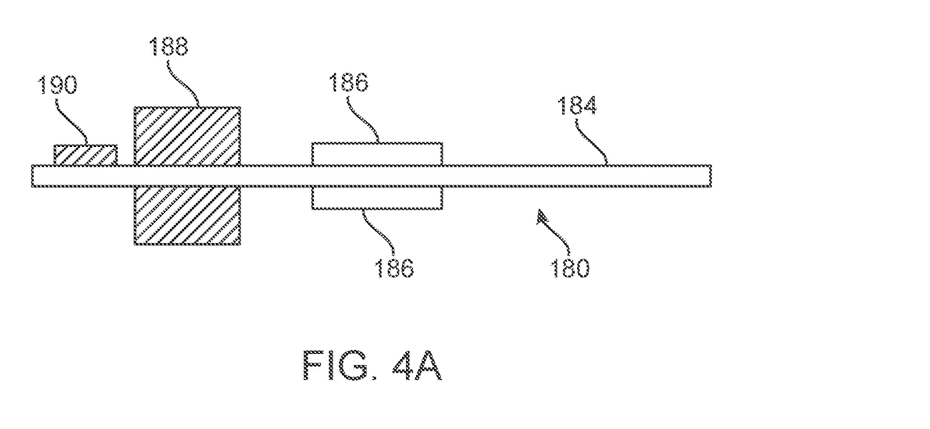
FIGS. 4A and 4B provide illustration of variations of strain devices for use with various movement detecting devices of the present disclosure.
Figure 4B:
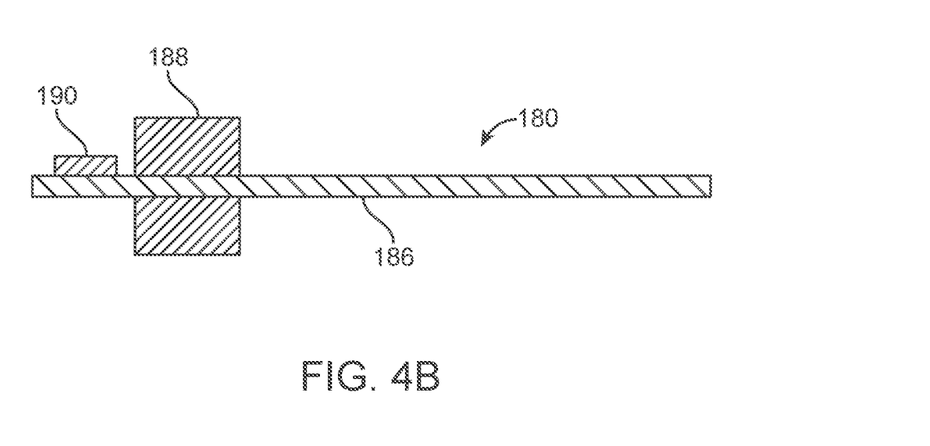

FIGS. 4A and 4B provide illustration of variations of strain devices 180 for use with various movement detecting devices of the present disclosure. FIG. 4A illustrates a strain device 180 comprising a deflectable base 184, fabricated from a metal, alloy, polymer, etc.). The deflectable base 184 will receive the strain inducing surface discussed herein such that movement of the strain inducing surface produces movement of the deflectable base 184. The deflectable base 184 is coupled to a piezo resistive or similar material 186 that allows detection of movement by producing a change in a resistance of the material 186 in response to a deflection of the material 186. In the variation depicted in FIG. 4A, the deflectable base 184 is coupled to an anchoring structure 188 and can include a temperature detecting element 190 for sensing a temperature. FIG. 4B shows another variation of a strain device 180 in which a piezo resistive or similar material 186 directly engages a strain inducing surface. The piezo resistive or similar material 186 is coupled to an anchoring structure 188 and can optionally include a temperature detecting element.

Figure 5:
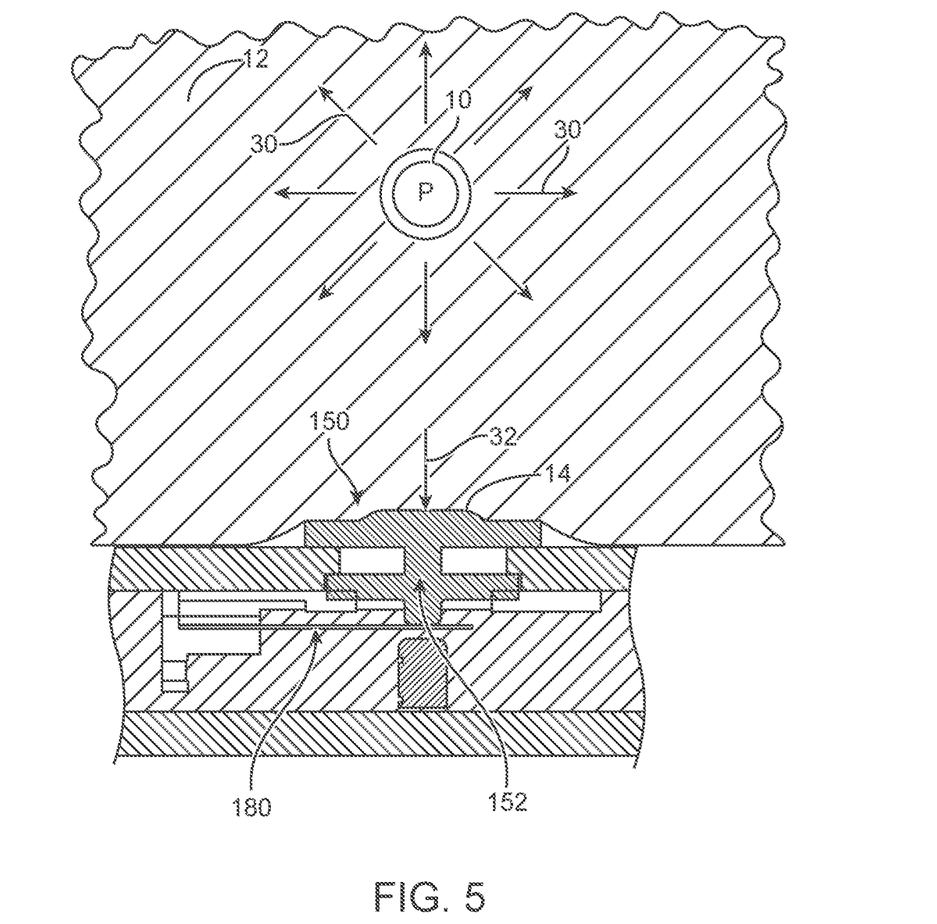
FIG. 5 is an illustration of a variation of a movement detecting apparatus applied to a region of tissue.

FIG. 5 is an illustration of a variation of a movement detecting apparatus 150 applied to a region of tissue 12. As noted above, the apparatus 150 can be used in a ring based body or other type of device. The region of tissue 12 will typically contain an artery 10 having pulsatile flow of blood therethrough. As a result of this blood flow, a pressure P within the vessel causes displacement of tissue that is adjacent to the artery 10. While the displacement is depicted by arrows 30, the displacement of adjacent tissue 12 will depend upon the anatomy that is in the vicinity of the artery 10. FIG. 5A illustrates a basic example of a tissue movement detecting apparatus 150 placed in contact with tissue 12 such that the contact member 152 compresses a region of adjacent tissue 14. Compression of the tissue increases the effect of tissue movement resulting from pressure P since the compressed region 14 is more prone to displacement and less likely to produce a cushion effect that would reduce deflection of the tissue. The displacement 30 caused by the artery 10 produces a radial displacement 32 adjacent to the contact member 152. As noted above, radial displacement 32 of the tissue 12 causes displacement of the contact member 152 to produce a displacement in the strain device 180. This allows for strain-gauge-based measurement of tissue movement that can be used to determine blood pressure. In effect, blood pressure P within the vessel 10 creates a radial displacement 32 or force that induces a strain in the strain device 180. The strain changes an electrical resistance of the strain device 180 which alters the current in the strain device 180 so that a voltage across the strain device 180 can be measured.

As noted above, the design of the contact member 150 is configured to transmit radial displacement 32 rather than circumferential displacement (e.g., displacement that is parallel to a plane of the tissue or perpendicular to a direction of the radial displacement).

Figure 6A:
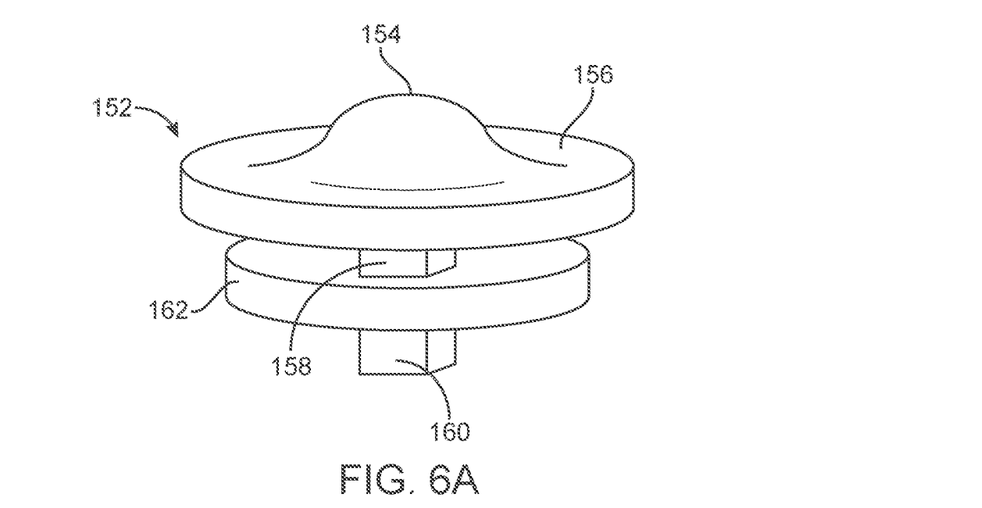
FIGS. 6A and 6B illustrate a contact member in respective undeflected and deflected states.
Figure 6B:
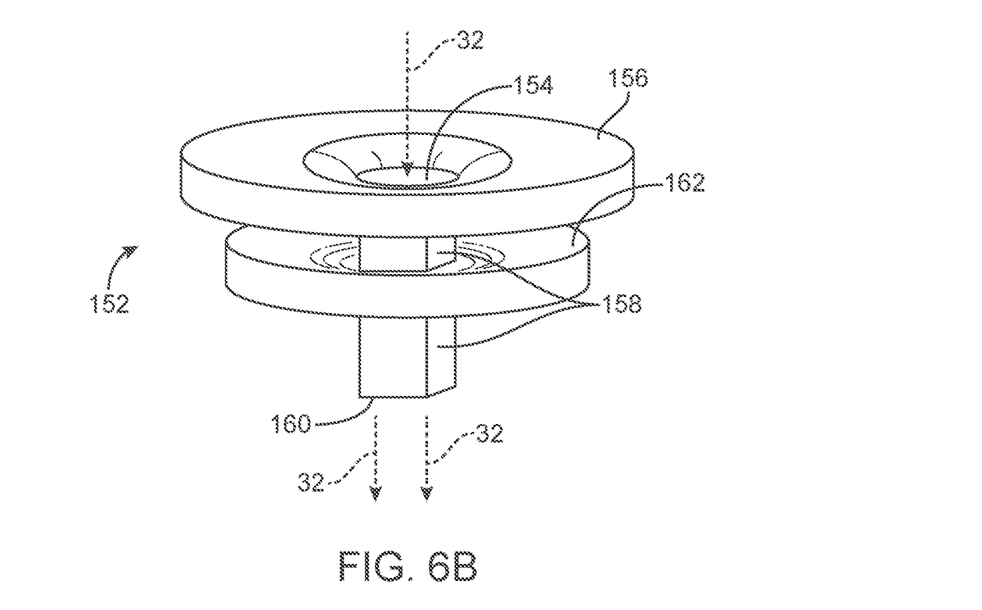

FIGS. 6A and 6B illustrate a contact member 152 in respective undeflected and deflected states. FIG. 6A illustrates a tissue engaging surface 154 located at a center of the contact member having a perimeter region 156 and a second perimeter region 162 located about the central region 158. As noted above, the perimeter regions 156 and 162 allow for securing the tissue contact member 152 within a body of the device. This construction also permits displacement of the tissue engaging surface 154 to produce displacement of the strain inducing surface 160 via movement of the central region. In one variation, the perimeter regions 156 and 162 are much softer/compliant as compared to the central region and tissue engaging surface. This design helps concentrate the radial force in the central area of the deformable skin contact 152.

FIG. 6B illustrates a state where the tissue contact member 152 is in a deflected state after tissue displacement 32 displaces the tissue engaging surface 154 causing the central region 158 and strain inducing surface to displace in the same direction as the tissue displacement 32. It is noted that this construction provides a radial force concentration construction that minimizes lateral or circumferential movement of the strain inducing surface 160 as a result of any lateral or circumferential forces applied by the tissue. Therefore, the radial displacement 32 of the strain inducing surface 160 alters a strain in the strain device (not shown in FIG. 6B) to produce a change in an electrical property of the strain device. This change in electrical property can be used to determine a change in a blood pressure of the associated artery.

Figure 7A:
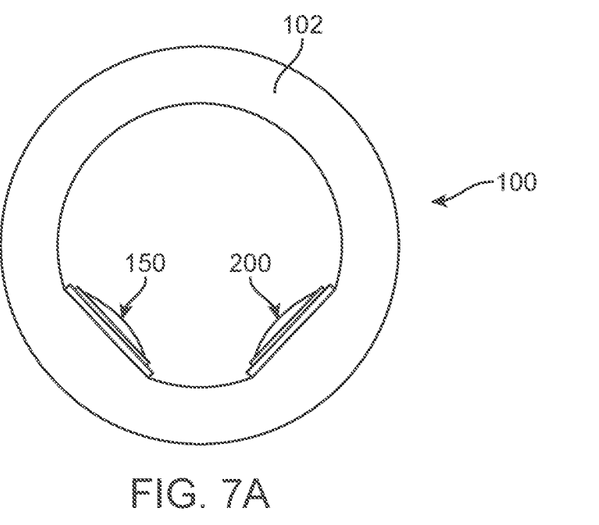
FIG. 7A illustrates another variation of a device in which there are at least a first movement detecting apparatus and a second movement detecting apparatus spaced apart on the ring body.
Figure 7B:
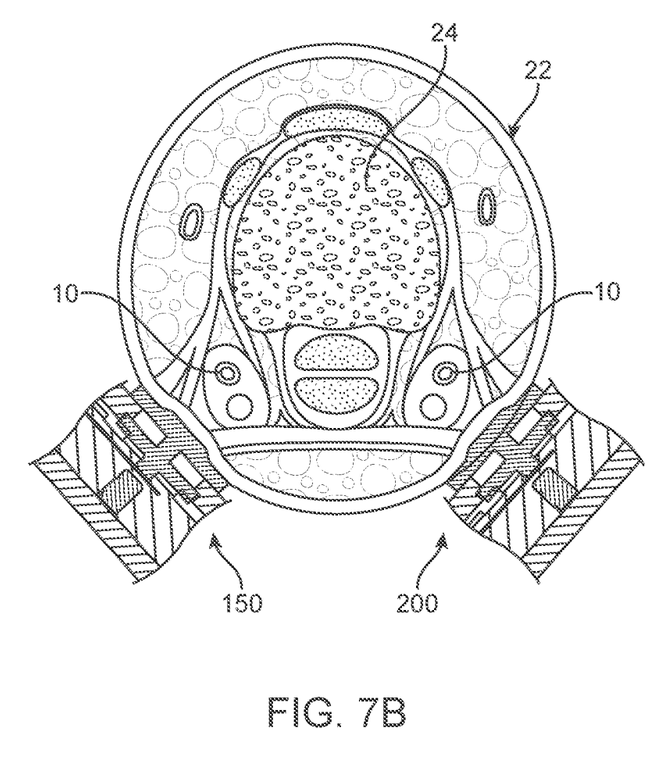
FIG. 7B illustrates the first movement detecting apparatus and a second movement detecting apparatus in relation to a finger.

FIG. 7A illustrates another variation of a device 100 in which there are at least a first movement detecting apparatus 150 and a second movement detecting apparatus 200 spaced apart on the ring body 102. FIG. 7B illustrates the first movement detecting apparatus 150 and a second movement detecting apparatus 200 in relation to a finger 22. As shown, each apparatus 150, 200 is placed adjacent to a vessel 10. However, alternative configurations and/or spacing are within the scope of this disclosure.

In one variation of the device, one or more movement detecting apparatus can be configured as a primary sensor that detects the radial force composed of the contact force the force induced by the blood pressure. A second sensor can be used to detect contact force to enhance the accuracy of the measurement. In such a case, blood pressure is determined by eliminating the contact force of the primary measurement. Moreover, the multiple apparatus configuration can be used to determine rotational error during positioning of the device. For example, gross rotation error can be detected by identifying the reduction of the blood pressure resulting from the rotation of the primary apparatus away from the artery and the increase of the blood pressure reading from the secondary apparatus.

Figure 8A:
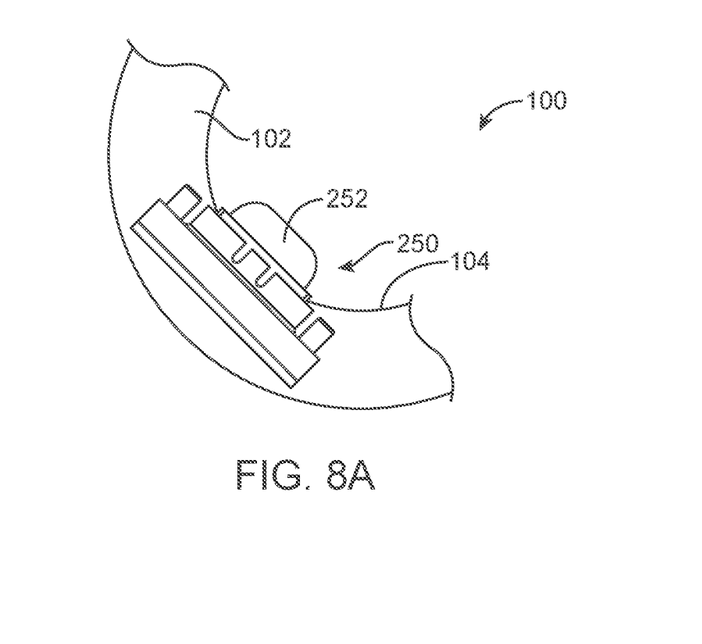
FIG. 8A illustrates a partial view of an additional variation of a device having a ring shaped body with a variation of a movement detecting apparatus.

FIG. 8A illustrates a partial view of another variation of a device 100 having a ring shaped body 102 with an inner surface 104 that includes a variation of a movement detecting apparatus 250. As shown, the apparatus 250 includes a tissue contact member 250 that protrudes beyond an interior surface 104 of the body 102. This variation of the apparatus 250 can be used in any of the devices discussed herein and can be used in combination with any other variation of a tissue movement detecting apparatus as described in this disclosure.

Figure 8B:
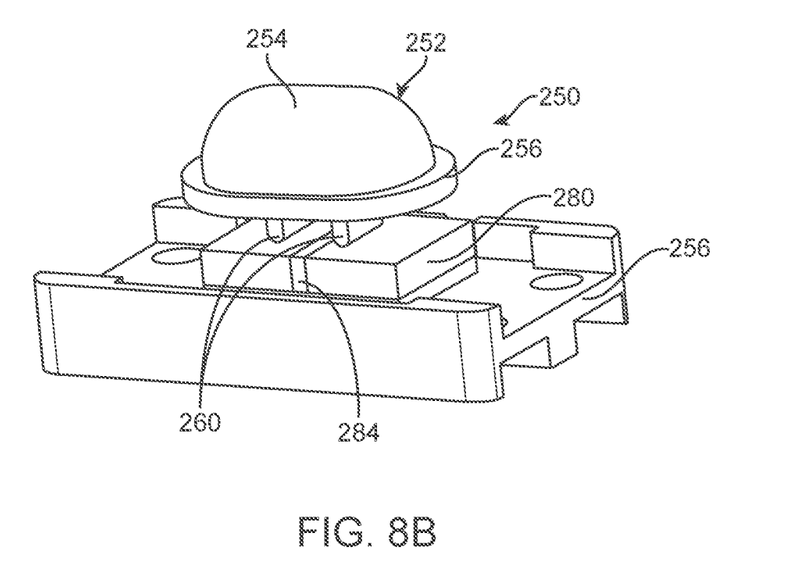
FIG. 8B illustrates the apparatus of FIG. 8A where the tissue contact member includes a tissue contacting surface with a perimeter region.

FIG. 8B illustrates the apparatus 250 of FIG. 8A where the tissue contact member 252 includes a tissue contacting surface 254 with a perimeter region 256. The tissue contacting surface 254 is connected to a strain inducing surface 260 as discussed below. The strain inducing surface 260 causes strain in a strain gauge upon deflection of the tissue contact surface 254. In the illustrated variation, a stress intensifier 284 is located adjacent to the strain inducing surface 260 and the strain gauge 280. The apparatus 250 can also include a base 254 for securing within the body of a device.

While FIG. 8B illustrates a single stress intensifier 284, the number of stress intensifiers 284 and stress inducing surfaces 269 between the deformable skin contact 252 and the strain gauge 280 can be varied. In other variations, the device does not require a strain intensifier.

Figure 8C:
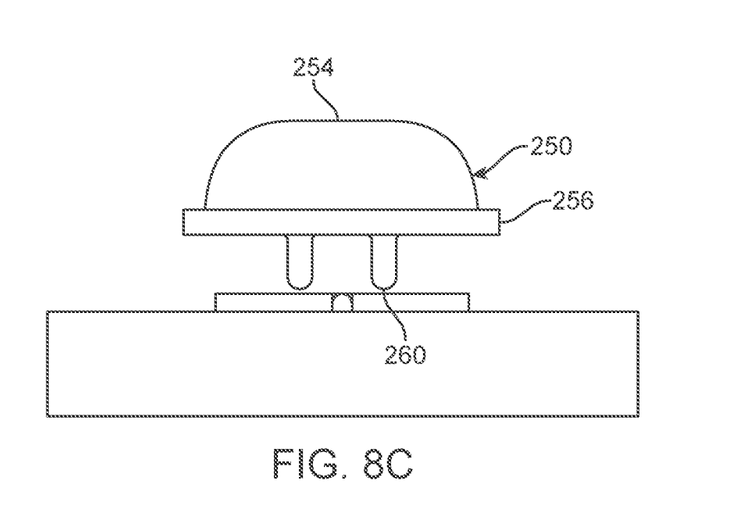
FIG. 8C and FIG. 8D illustrates respective side and cross sectional views of the apparatus of FIG. 8B.
Figure 8D:
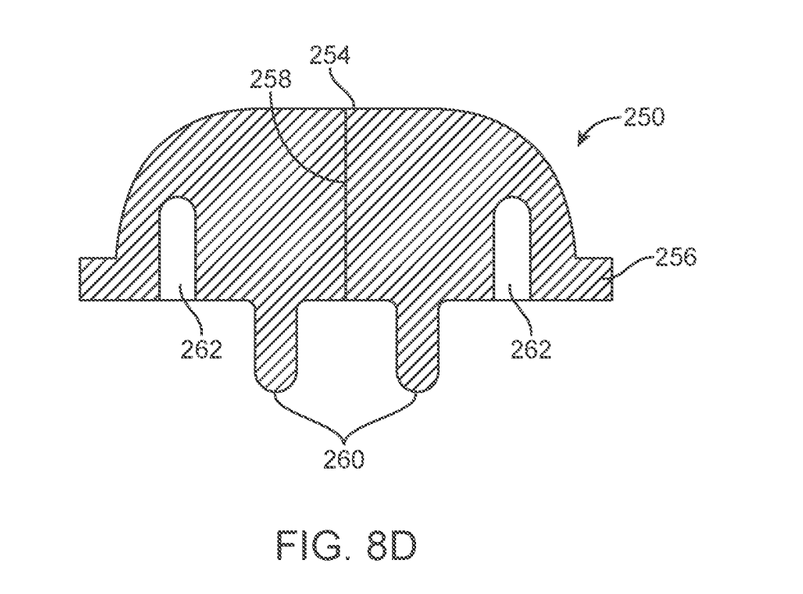

FIG. 8C and FIG. 8D illustrates respective side and cross sectional views of the apparatus 250 of FIG. 8B. As shown in FIG. 8D, the tissue contact member 250 comprises a radial concentration construction as the central region 258 is surrounded by a cavity 262 that increases the ability of the tissue contact surface 254 to transmit radial displacement of tissue to the stress inducing surfaces 260 as discussed above.

Figure 9A:
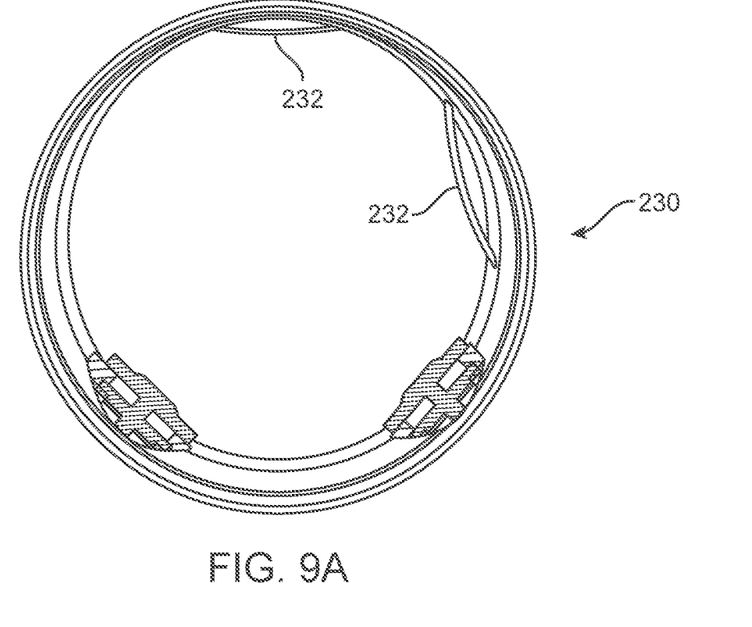
FIGS. 9A and 9B illustrate devices and that incorporate adjustability features to properly align the movement detecting components relative to a digit.
Figure 9B:
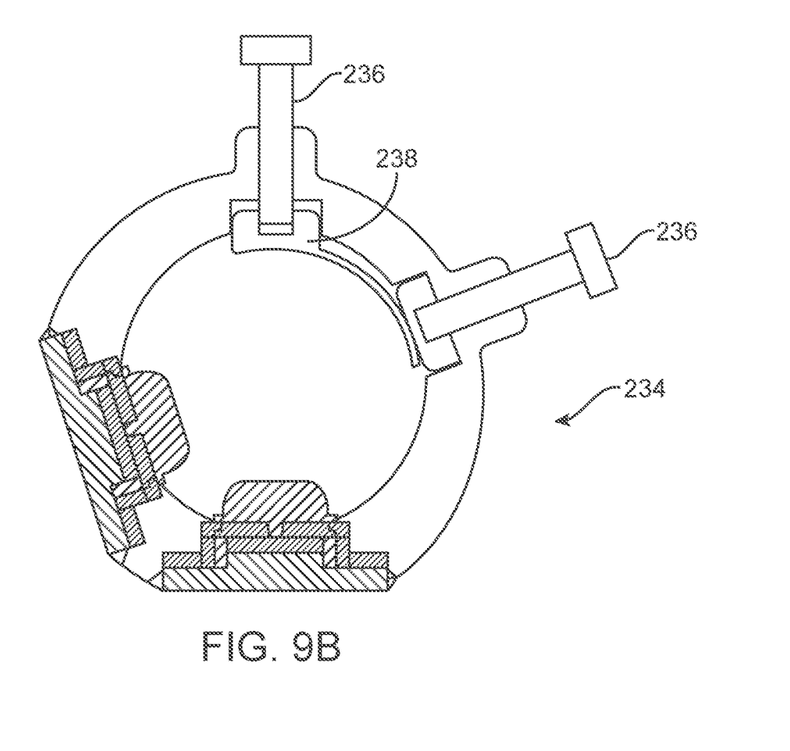

FIGS. 9A and 9B illustrate devices 230 and 234 that incorporate adjustability features to properly align the movement detecting components relative to a digit. Alternatively, or in combination, the adjustability features can adjust the degree to which the tissue contacting surface compresses adjacent tissue. FIG. 9A illustrates a first and second spring such as a leaf spring 232. One or both leaf springs 238 can be adjustable as needed. FIG. 9B illustrates a device 234 as having an inner spring surface 238 that is adjustable by one or more screws 236. One or both of the screws 236 can push the digit toward one of the sensors and/or loosen the device about the digit. Also, the inner spring surface 238 can form a smooth and movable inner surface to adjust the inner radius of the ring.

In practical use, while wearing the wearable device and measuring the blood-pressure thereby, the monitoring surfaces are preferentially placed at the lower section of the wearable device at the location of the artery besides the bone lays in an embodiment of the present invention. Therefore, the deformations of the skin due to blood pulse struck directly upon the strain gauge producing the maximum strain and signal. In a preferred embodiment, a more accurate measured blood-pressure can be retrieved if the wearer relaxes.

As described above, according to the embodiments of the present invention, a strain-gauge and pressure sensor are mounted on the inner surfaces of the wearable devices which can calculate the blood pressures based on the surface deformations due to the variations of finger arteries. Accordingly, the wearable devices and the monitoring methods according to the embodiments of the present invention are expected to be beneficial for real-time monitoring of patients and bio-medical applications.

Further, the wearable device has light-weight and compact volumes and is comfortable for human beings to wear. Thus, the wearable device is suitable for long-time wearing and accordingly long-term blood-pressure monitoring.

In addition, since the arteries at finger are close to the skin surface, such ring-shaped wearable device can measure the blood-pressure easier. Also, by measuring the blood-pressure directly on the skin surface close to the arteries in a form of deformation of the surface, the accuracy of the measured blood-pressure can be increased. In certain embodiments of the present invention, the signal representing the deformation of the surface can be directly represented as the electrical resistance, thus simplifying the following signal processing procedures in the electronic device since it is already an electrical signal form.

Although the present invention has been described with reference to the preferred embodiments thereof, it will be understood that the invention is not limited to the details thereof. Various changes and modifications in accordance with the appropriate technical solutions and technical concepts of the present invention should belong to the invention as claimed. Therefore, all such substitutions and modifications are intended to be embraced within the scope of the invention as defined in the appended claims.

Well-known structures, materials, or operations are not shown or described in detail to avoid obscuring aspects of the described devices. As those skilled in the art would realize, the described embodiments may be modified in various different ways, all without departing from the spirit or scope of the present invention. It should be noted that, without conflict, in the embodiment of the present invention and examples of features can be combined with each other. Therefore, it should be appreciated that the embodiments described herein are not intended to be exhaustive of all possible embodiments in accordance with the present disclosure, and that additional embodiments may be conceived based on the subject matter disclosed herein.

We claim:

1. A device for monitoring blood pressure in a blood vessel of a body member using a tissue adjacent to the blood vessel, the device comprising:
    a device body configured to extend at least partially about the body member, the device body having an interior surface adapted to be positioned adjacent or in contact with a surface of the body member;
    a tissue movement detecting assembly positioned on or in the device body, the tissue movement detecting assembly comprising a strain device; and
    a contact member formed as a single piece and comprising a perimeter region and a central region, the contact member adjacent to the device body and positioned to engage a surface of the tissue, where the central region of the contact member forms a tissue engaging surface protruding beyond the perimeter region of the contact member such that when the device body is positioned adjacent to tissue, the perimeter region and the central region contact the tissue to compress the tissue, the contact member also having a strain inducing surface extended from a surface opposite to the tissue engaging surface and adjacent to the tissue movement detecting assembly;
    wherein a compliance of the perimeter region differs from a compliance of the central region to cause the central region to transmit displacement of the contact member to a greater degree than the perimeter region such that, when the tissue engaging surface engages the tissue, displacement of tissue in a radial direction relative to the tissue caused by a change in a pressure in the blood vessel also displaces the tissue engaging surface causing displacement of the central region of the contact member in the radial direction so that the strain inducing surface alters a strain in the strain device to produce a change in an electrical property of the strain device.

2. The device of claim 1, wherein the contact member comprises a double layer structure having a first layer adjacent to the tissue engaging surface and a second layer spaced from the first layer, wherein where the first and second layer are joined by the central region of the contact member.

3. The device of claim 1, wherein where the device body comprises a cavity that nests the contact member.

4. The device of claim 1, further comprising a power supply electrically coupled to the tissue movement detecting transducer assembly.

5. The device of claim 1, wherein the contact member is configured such that the perimeter region of the contact member is reinforced such that the perimeter region transmits displacement less than the central region of the contact member.

6. The device of claim 1, wherein the contact member is configured such that the perimeter region of the contact member is weakened to cause the central region to displace in the radial direction by flexure of the perimeter region.

7. The device of claim 1, wherein the contact member is configured such that the perimeter region of the contact member is softer than the central region such that the central region transmits displacement greater than the perimeter region.

8. The device of claim 1, wherein the contact member comprises at least one cavity below the tissue engaging surface, wherein where the at least one cavity extends about the central region, wherein the at least one cavity causes the perimeter region of the contact member to be softer relative to the central region which improves an ability of the central region to transmit displacement.

9. The device of claim 1, wherein the strain inducing surface comprises at least one protrusion, wherein displacement of the central region of the contact member causes the at least one protrusion to alter the strain in the strain device.

10. The device of claim 9, further comprising a displacement limiting stop structure adjacent to the at least one protrusion, wherein where the displacement limiting stop structure limits movement of the strain inducing surface.

11. The device of claim 1, further comprising a displacement limiting stop structure adjacent to the at least one strain device wherein where the displacement stop structure limits movement of the strain device.

12. The device of claim 1, wherein the tissue movement detecting transducer assembly comprises a deformable base adjacent to the strain device, wherein where the deformable base permits deformation of the strain device.

13. The device of claim 12, wherein the deformable base comprises an elastomer.

14. The device of claim 12, further comprising at least one protrusion adjacent, inside, or through the deformable base that increases deflection of the strain device.

15. The device of claim 1, wherein the contact member is elastically deformable.

16. The device of claim 1, wherein the tissue movement detecting transducer assembly and contact member form a primary sensor, the device further comprising a secondary sensor comprising a second contact member and a second tissue movement detecting transducer assembly, wherein the secondary sensor is spaced a distance from the primary sensor on the interior surface of the device body.

17. The device of claim 1, wherein where the strain device comprises at least a strain gauge or a conductive polymer.

18. The device of claim 1, wherein the strain device comprises a first strain gauge and a second strain gauge.

19. The device of claim 18, wherein the first strain gauge is positioned on a first side of a deflectable base and wherein where the second strain gauge is positioned on a second side of a deflectable base, wherein where a fixed end of the deflectable base is coupled to an anchoring structure and a free end of the deflectable base is positioned adjacent to the strain inducing surface.

20. The device of claim 1, wherein the device body comprises a shape selected from the group consisting of a cylinder shape, a partial cylinder shape, a ring shape, an oval shape, and a non-cylinder shape.

21. The device of claim 1, wherein the device body comprises a spring biasing member configured to bias the device body against the body member to cause the contact member to at least engage tissue of the body member.

22. A device for monitoring blood pressure in a blood vessel using a tissue adjacent to the blood vessel, the device comprising:
a device body;
a tissue movement detecting assembly positioned in the device body, the tissue movement detecting assembly comprising a strain device; and
a contact member formed as a single piece and having a tissue engaging surface protruding beyond a surface of the device body such that when the device body is positioned adjacent to tissue, the contact member compresses the tissue, the contact member also having a strain inducing surface extended from a surface opposite to the tissue engaging surface and adjacent to the tissue movement detecting assembly;
wherein the contact member comprises a perimeter region and a central region, where a compliance of the perimeter region differs from a compliance of the central region to cause the central region to transmit displacement of the contact member to a greater degree than the perimeter region such that, when the tissue engaging surface engages the tissue, displacement of tissue in a radial direction relative to the tissue caused by a change in a pressure in the blood vessel also displaces the tissue engaging surface causing displacement of the central region of the contact member in the radial direction so that the strain inducing surface alters a strain in the strain device to produce a change in an electrical property of the strain device.

* * * * *